United States Patent [19]

Wrigley

[11] Plant 4,615

[45] Jan. 6, 1981

[54] APPLE TREE

[76] Inventor: Irving H. Wrigley, 2550 Wrigley Rd., Eureka, Calif. 95501

[21] Appl. No.: 36,787

[22] Filed: May 7, 1979

[51] Int. Cl.[3] ..... A01H 5/03
[52] U.S. Cl. ..... Plt./34
[58] Field of Search ..... Plt./34

[56] References Cited

PUBLICATIONS

The Apples of New York, Beach, 1905, J. B. Lyon Co., Albany, pp. 345-349 cited.

*Primary Examiner*—Robert E. Bagwill
*Attorney, Agent, or Firm*—Ronald M. Anderson

[57] ABSTRACT

This invention relates to a mutation of the Tompkins King strain of apple tree, and differs therefrom by the solid red coloring of the fruit produced thereby.

2 Drawing Figures

1

BACKGROUND

This invention is a new and distinct variety of apple tree. It was discovered by applicant at his farm in Section 26, Township 4 North, Range 1 West, Humboldt County, Calif. It is a limb mutation of Tompkins King, and was asexually reproduced by applicant through grafting it to M 7 rootstock. The resulting tree is growing on applicant's farm at 2550 Wrigley Road, Eureka, Calif.

The new variety produces fruit that is colored a solid red, without contrasting yellow undercover or background, differing thereby from the red fruit of the Tompkins King strain, which may be accurately described as colored a "fine yellow, mottled and washed with orange red, and splashed with bright carmine." (Ref. - *Apples of New York* Beach—1905 Edition).

BRIEF DESCRIPTION OF THE DRAWINGS

(Color Photographs)

FIG. 1 shows a typical example of the fruit and foliage of the new solid red Tompkins King variety.

FIG. 2 shows a typical example of the fruit of the new variety on the left, and for comparison, a typical example of the fruit of the original Tompkins King strain on the right, both examples being grown under similar conditions of cultivation, on the same type rootstock.

TECHNICAL DESCRIPTION

TREE

Habit: The tree is vigorous in growth, with upright, spreading, and open form. Lateral branches are usually slender and somewhat drooping. The spurs are fairly stout. Internodes on new wood are fairly long.

Bark: The bark is greyish brown. Lenticels are tan, lightly raised, fairly numerous, small, round to elongated in shape.

2

Leaves

Color: Leaves are medium dark green.

Shape: Their shape is ovate and pointed.

Size: Average size is 3½ to 4 inches long by 2½ to 3 inches wide. The stems average 1 in length.

Margin: The edges are unevenly serrated.

Veining: Rib and veins are lightly pink colored.

Flowers

Buds: Fruit buds are large and stubby to pointed in shape, and pubescent.

Fruit

Shape: The fruit is large and fairly uniform in shape, being round to somewhat oblate in form.

Stem: The stem is short to medium long in length, tending to be thick in diameter. The cavity around the stem is medium to small, shallow to moderately deep, and sometimes narrowly russetted.

Basin: The basin is small to medium.

Color: The prevailing color is substantially solid red, in the color range described by Hue 7½, chips Pc, Pa, and Pe, reference Color Harmony Charts, and Manual of Names, (Ostwald System, Munsell Notation), Published by Container Corporation of America, Edited by Taylor, Knucke, and Granville.

Flesh: Color of the flesh is faintly yellow. Its texture is crisp and it has been characterized as tender, juicy, and sub-acid, with a very good strong flavor.

Aroma: The apple has a freshly pleasant faint aroma.

Keeping quality: Considered to keep fairly well.

Season: October.

Use: The apple is suitable for use as a dessert eating apple and for all types of cookery.

I claim:

1. A new and distinct variety of apple tree, substantially as described in this application, and in particular, characterized by the solid red colored fruit which it bears.

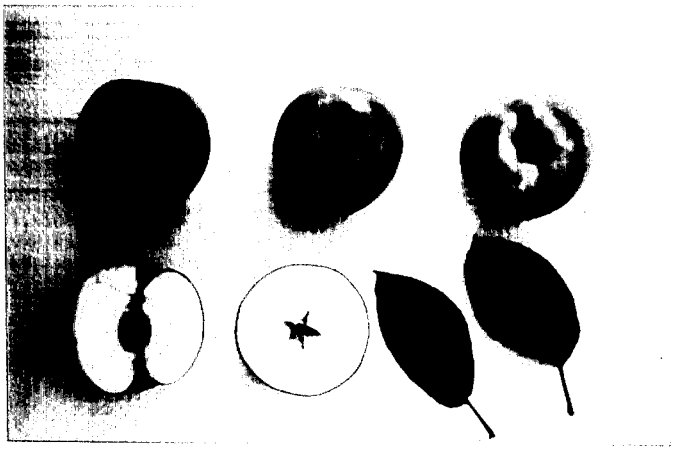
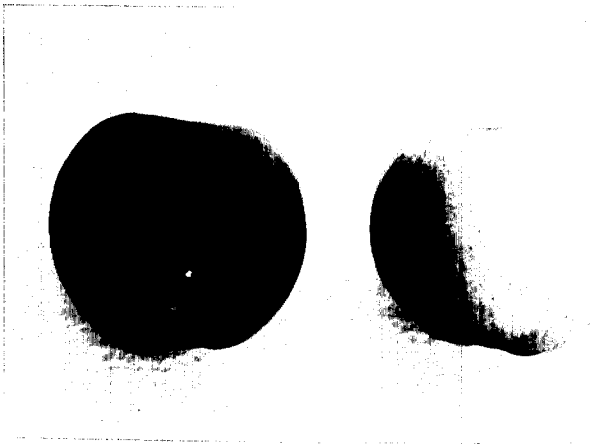

* * * * *